United States Patent [19]
Tonna

[11] Patent Number: 5,240,108
[45] Date of Patent: Aug. 31, 1993

[54] SHARPS DISPOSAL SYSTEM

[75] Inventor: Patrick R. Tonna, San Jose, Calif.

[73] Assignee: Kaiser Foundation Hospitals, Oakland, Calif.

[21] Appl. No.: 827,554

[22] Filed: Jan. 28, 1992

Related U.S. Application Data

[63] Continuation of Ser. No. 617,831, Nov. 26, 1990, abandoned.

[51] Int. Cl.⁵ .............................................. B65D 83/10
[52] U.S. Cl. .................................. 206/366; 206/364; 206/365; 211/84
[58] Field of Search ............... 206/366, 370, 364, 365; 229/117.12; 211/4, 84, 88, 181

[56] References Cited

U.S. PATENT DOCUMENTS

| | | | |
|---|---|---|---|
| 3,096,883 | 7/1963 | Llewellyn | 211/106 X |
| 3,346,318 | 10/1967 | Propst | 229/117.12 X |
| 3,420,483 | 1/1969 | Stalker | 211/88 X |
| 3,563,505 | 2/1971 | Langley | 211/84 X |
| 3,591,120 | 7/1971 | Fietzer | 211/106 X |
| 4,576,281 | 3/1986 | Kirksey | 206/370 |
| 4,674,676 | 6/1987 | Sandel et al. | 206/366 X |
| 4,726,477 | 2/1988 | Martin | 211/181 X |
| 4,736,860 | 4/1988 | Bemis | 220/908 X |
| 4,756,504 | 7/1988 | Chamberlain | 211/4 X |
| 4,826,073 | 5/1989 | Bruno | 206/366 X |
| 4,869,366 | 9/1989 | Bruno | 206/366 X |
| 4,911,294 | 3/1990 | Russo et al. | 206/366 |
| 4,930,631 | 6/1990 | Bruno | 206/366 |
| 4,955,477 | 9/1990 | Bruno | 206/366 |
| 4,969,554 | 11/1990 | Sawaya | 206/366 |
| 5,067,223 | 11/1991 | Bruno | 206/366 X |
| 5,076,429 | 12/1991 | Patrick et al. | 206/370 |

OTHER PUBLICATIONS

*Fibre Box Handbook,* Fibre Box Association, Chicago, 1984, pp. 35-36.
Sage Products, Inc. advertising flyer "Sharps Disposal System," copyright, 1988.
Becton Dickinson advertising flyer for nestable sharps collectors, copyright 1989.
Winfield Industries ordering information sheet, in existence since at least Jul. 1990.
Occupational Safety and Health Reporter, pp. 459, 460, Aug. 15, 1990.

*Primary Examiner*—David T. Fidei
*Assistant Examiner*—BethAnne C. Cicconi
*Attorney, Agent, or Firm*—Townsend and Townsend Khourie and Crew

[57] ABSTRACT

A sharps disposal system (2) includes a fiberboard container (6) mounted to a wall (8) by a lockable cage (4). The container has an entrance opening (70) formed through the top (20), sized for the deposit of sharps into its interior. A baffle (60) extends within the interior from the back downwardly and forwardly and is sized and positioned to discourage manual access to the interior while directing sharps into the interior. The container also includes a lid (84) hinged to the top for movement between stable opened and closed positions to permit one hand operation when opened. For disposal the lid is secured to the top using a foam adhesive strip (104) to provide a secure, substantially leakproof seal. The container is coated on the inside surface with a hydrophobic material and has the seams and corners sealed to make the interior of the container substantially leakproof. A view port (50) can be provided to permit the user to determine when the container is full. Handles (126) extend from the top to aid lifting the container from the wire cage and help prevent inadvertent sticks in the unlikely event that a needle or other sharp object has pierced the container.

21 Claims, 4 Drawing Sheets

SHARPS DISPOSAL SYSTEM

This is a division of application Ser. No. 07/617,831 filed Nov. 26, 1990, now abandoned.

BACKGROUND OF THE INVENTION

Safe disposal of needles, syringes, IV sets, vials and other medical products, typically termed "sharps" because of their sharp edges or points, has become increasingly important, largely due to the presence of AIDS. An inadvertent needle stick, while never a desirable thing and often dangerous, now can be life threatening. Although needles, syringes and so forth are usually packaged to be relative safe prior to use, after use the products often exposed sharp edges or pointed tips. Handling and disposal of the sharps create acute problems for health care professionals, housekeepers and central supply personnel.

Because of the problems created by infectious waste, particularly sharps, various types of sharps disposal systems have been developed. A common practice is to use a plastic container having a door which operates much like the door on a conventional mailbox. To use the system, one opens the hinged door with one hand, drops the sharps into the opening and then closes the door; this allows the sharps to drop into a plastic bag within the interior of the container for later disposal. This solution, while addressing many of the safety concerns, requires the use of both hands to dispose of the sharps. This may be difficult or inconvenient to do and can expose the health care worker to infectious material. In addition, such systems require extensive handling of the plastic bag liners, and workers responsible for disposal of the used sharps are subjected to risks of needle sticks when they remove the plastic bags of sharps from the container and handle the bags during transport. Also, further environmental problems are created if one were to incinerate or otherwise dispose of the plastic container along with the sharps and medical waste contained therein.

SUMMARY OF THE INVENTION

The present invention is directed to a sharps disposal system especially suited for disposal of infectious medical waste through the use of a substantially leakproof container which permits one-handed operation and allows the container and the medical waste within the container to be incinerated together.

The sharps disposal system includes a container, typically a rectangular box, having a top with an entrance opening sized for the deposit of sharps, such as used syringes, therethrough for containment within the interior of the container. The container also includes a baffle positioned within the interior of the container. The baffle extends from the back side of the container downwardly and forwardly to lie beneath the opening. The baffle is sized and positioned to discourage manual access to the interior of the container while directing sharps dropped through the entrance opening into the interior. The baffle is also sized and positioned to help prevent the contents of the container from falling out if the container is inadvertently dropped or tuned upside down during handling.

The container also includes a lid hinged to the top for movement between stable opened and closed positions. That is, when the hinged lid is in the open position, it remains open without effort on the part of the user. This enables the user to drop a sharp into the container using only one hand since nothing needs to be manipulated. The closed position is also a stable position so that once the container is closed, typically prior to disposal, it will not inadvertently open. For disposal, the lid is preferably adhesibly secured to the top, preferably using a foam adhesive strip secured to either the lid or the top and circumscribing at least a part of the opening. This helps provide a secure, leakproof seal. The container is preferably made of fiberboard coated on the inside surface with a hydrophobic material so that any liquid from the sharps does not leak through. The outside of the container is preferably coated to aid cleaning. The container may be a substantially one piece folded box with the seams and corners sealed to make the interior of the container substantially leakproof.

The container preferably includes handles which are integral extensions of the top. These enable the container to be handled without requiring the container to be touched, thus reducing the possibility of inadvertent needle sticks.

A wire cage is preferably used to secure the container to a support surface, such as a wall, to make the container readily available. The wire cage is lockable to prevent unauthorized removal of the sharps container. The cage is constructed so that the lid can be moved between the open and closed positions while still within the cage so that the sharps box can be closed and sealed before being removed from the cage for additional safety.

The container preferably includes a view port to permit the user to determine when the container is full. Handles, preferably extending laterally away from the top, are preferably provided to aid lifting the container from the wire cage and shaking down the contents for a better fill. This also helps prevent inadvertent sticks in the unlikely event that a needle or other sharp object has pierced the container.

An absorptive material can be used on the bottom of the container to absorb any liquid leaks from the sharps. A tapered needle separation slot can be formed in the container, and preferably in the top at a location which can be sealed by the lid upon disposal. This slot can be used to assist in the removal and disposal of a needle assembly from the barrel of a syringe without requiring the needle assembly to be grasped by the user.

Other features and advantages of the invention will appear from the following description in which the preferred embodiment has been set forth in detail in conjunction with the accompanying drawings.

DESCRIPTION OF THE PREFERRED EMBODIMENT

Figure 1:
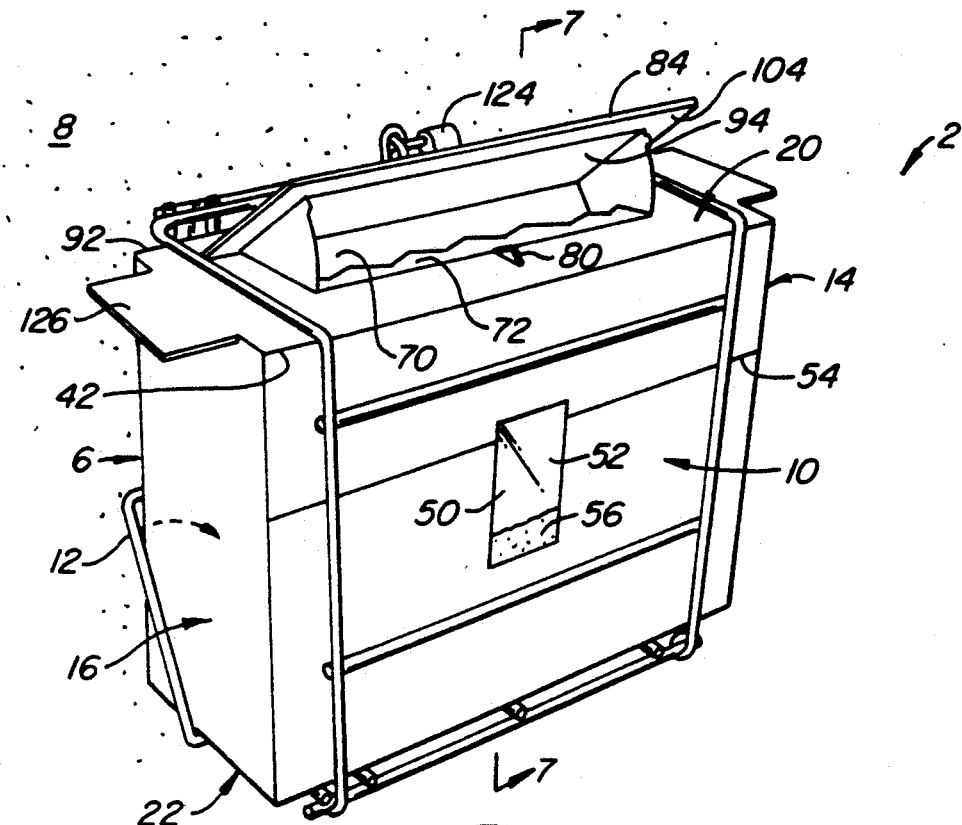
FIG. 1 is a perspective view of a sharps disposal system made according to the invention.

FIG. 1 illustrates a sharps disposal system 2 including a cage 4 supporting a container 6 adjacent a vertically oriented wall 8. Container 6 is a folded fiberboard container preferably made of fiberboard such as is made by the Longview Fiber Co. of Oakland, Calif., under product designation 249. This fiberboard is preferred because it is puncture resistant, can be incinerated in an environmentally safe manner, and meets various criterion for resistance to the spread of flame, such as UL49HB.

The inside of container 6 is coated with a hydrophobic material to help make it substantially leakproof. One such coating is made by Michelman Chemicals, Inc. of Cincinnati, Ohio under the designator Coating X-300. The outside of container 6 is preferably coated with paraffin to aid keeping the outside clean.

Referring the reader to FIGS. 2-7, container 2 is seen to include a front 10, a back 12, a right lateral side 14 and a left lateral side 16, all created from a single container blank 18. Container blank 18 also defines the top 20 and the bottom 22 of container 6, bottom 22 including and a pair of bottom flaps 24, 26. The various parts of container blank 18 are folded over at the various fold lines 28 using a suitable waterproof adhesive, such as Jet-Melt TM adhesives made by 3-M of St. Paul, Minn. as product nos. 3738, 3762, and 2762-LM. When doing so, the outside surface of side flap 30 is adhered to the inside surface of left lateral side 16. The use of short bottom flaps 32, 34 positioned on the inside of bottom flaps 24, 26 helps to create a substantially leakproof seal at bottom 22 of container 6. Similarly, short top flaps 36, 38 come together with main top flap 40 help provide a substantially leakproof edge 42 circumscribing top 20. The interior corners are preferably filled with the adhesive to help create leakproof joints.

Figure 3:
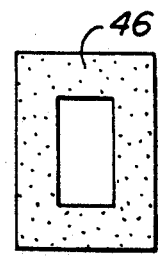
FIGS. 2-6 are plan views of the blanks of the main components of the container of FIG. 1 prior to folding.
Figure 6:
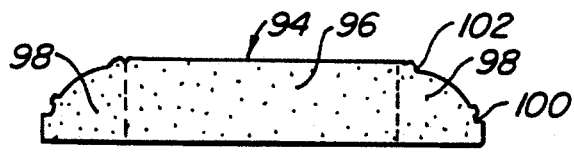

FIG. 3 illustrates a window reinforcement 46 which is secured to the inside surface 48 of front 10 surrounding view port 50. Reinforcement 46 also helps to secure transparent covering 52 (see FIGS. 1 and 7) to inside surface 48. Transparent covering 52 is preferably a polycarbonate material, such as sold under the trademark LEXAN TM by General Electric Co. of Pittsfield, Mass. Use of covered view port 50 allows the user to determine when container 6 is filled. The fill line is preferably marked on the front 10 as shown by line 54 in FIG. 1.

Since it is preferable that container 6 be substantially leakproof, it is important to get a good adhesive seal between transparent covering 52 and inside surface 48. To help ensure the proper adhesion between the surfaces, the extent of the adhesive contact between covering 52 and inside surface 48 can be visually observed through transparent covering 52 during manufacture but before window reinforcement 46 is mounted to inside surface 48.

Figure 7:
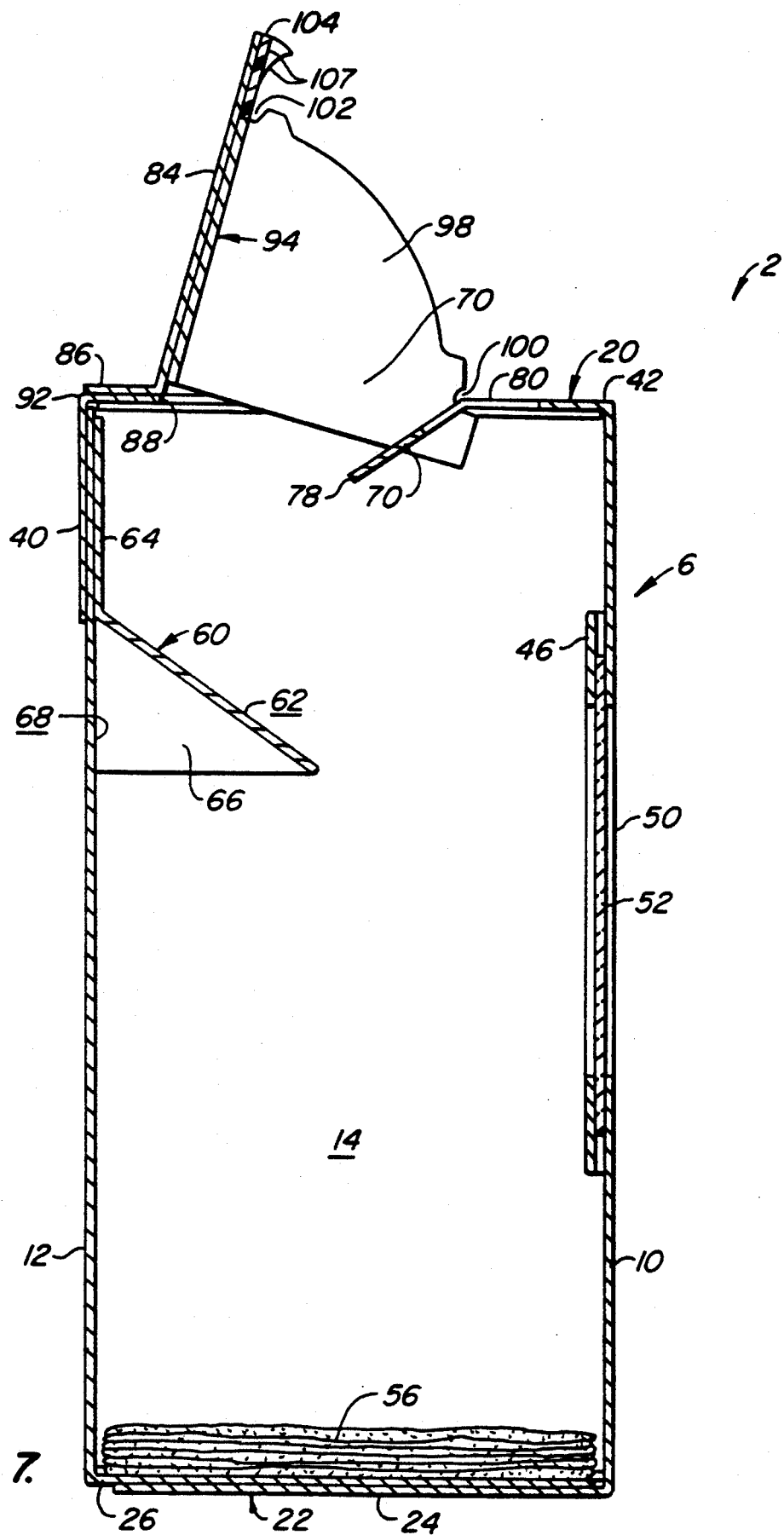
FIG. 7 is a cross-sectional view of the container of FIG. 1.

An absorbent pad 56, shown in cross section in FIG. 7, is preferably secured within the interior of container 6 on bottom 22. Pad 56 is preferably impregnated with a substance to kill or control the growth of bacteria and other undesirable organisms within container 6.

Figure 4:
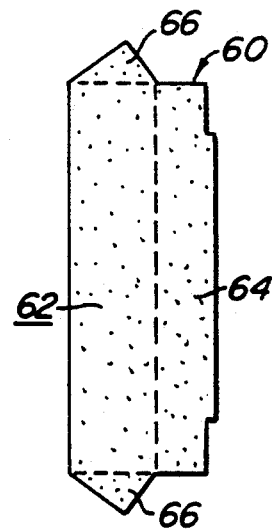

Prior to securing main top flap 40 to the outer surface of back side 12, a baffle 60, shown prior to folding in FIG. 4, is mounted within container 6. Baffle 60 includes a baffle surface 62, an adhesive flap 64 and a pair of positioning wedges 66 extending from the lateral sides of baffle surface 62. As shown in FIG. 7, adhesive flap 64 is secured to the inside surface 68 of back side 12 while positioning wedges 66 limit the angle at which baffle surface 62 extends downwardly and forwardly, that is towards front side 10 and bottom 22. Baffle 60 helps deter individuals from manually accessing the contents of container 6 by having baffle surface 62 positioned directly beneath entrance opening 70 formed in top 22. Baffle 60 also helps prevent the contents of the container 6 from falling out if the container 6 is inadvertently dropped or turned upside down during handling. Entrance opening 70 also has a downwardly and rearwardly extending guide flap 72 extending from its forward edge 76. Guide flap 72 has a scalloped outer edge 78 which further helps deter the user from inserting his or her hand into the interior of container 6.

Top 22 also includes a needle separation slot 80 formed along forward edge 76. Slot 80 is tapered to assist in the removal of a needle assembly from the barrel of a syringe and the deposit of the needle assembly into the container without requiring the user to touch the needle assembly.

Figure 5:
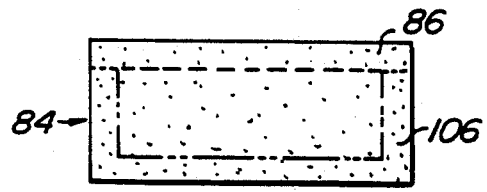
Figure 8:
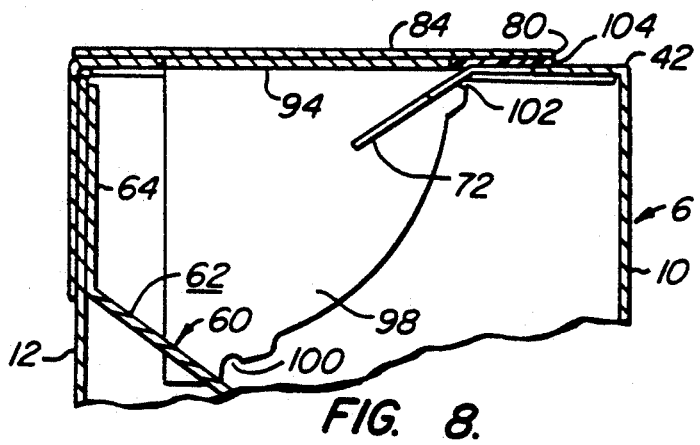
FIG. 8 is a cross-sectional view of a portion of the container of FIG. 1 showing the lid in the closed position.
Figure 2:
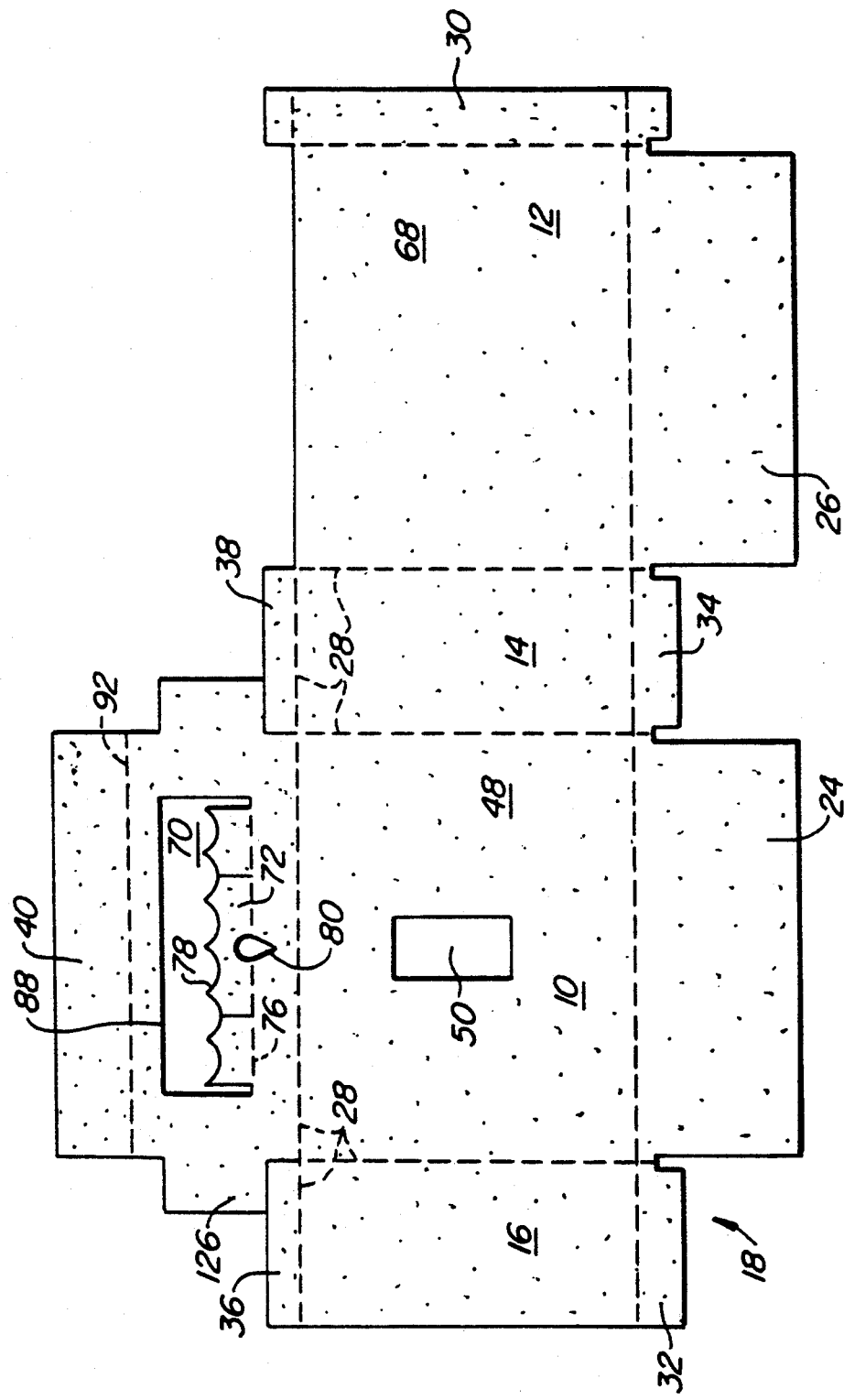

Container 6 also includes a hinged lid 84, shown as a blank in FIG. 5. Lid 84 includes a lid flap 86 which is secured using an adhesive between the rear edge 88 bounding entrance opening 70 and the back portion 92 of top edge 42. A lid stop 94, see FIG. 6, includes a main portion 96 secured to the underside of lid 84 with an adhesive and a pair of detented guides 98 extending at about 90° angles from main portion 96. Guides 98 each include open and closed detents 100, 102 which, when engaging edge 76, help keep lid 84 in the open position of FIGS. 1 and 7 and in the closed position of FIG. 8. With lid in the open position of FIGS. 1 and 7, the user can simply drop the sharps through opening 70, a simple, one-handed procedure.

Lid 94 has a resilient, self-stick sealing strip 104 placed in a U-shaped region 106, outlined in phantom lines in FIG. 5. Sealing strip 106 is preferably resilient to provide a better seal between lid 94 and top 22. An example of one such adhesive strip is made by the Decco Felt/Fasson Division of Avery Products of Painsville, Ohio under the product designation no. 2116 double sided foam tape. When it is time to seal entrance opening 7, the protective film liner 107 is removed from adhesive sealing strip 104, lid 84 is moved to the closed position of FIG. 8 and pressed against top 22 to create a substantially waterproof, secure seal over entrance opening 70. As suggested in FIG. 1, this can take place while container 6 is secured within cage 4 so that container 6, plus its contents, can be sealed prior to being removed from the cage. If desired, a wide sealing tape can be placed over lid 84 on top 22 to provide additional deterrence against inadvertent or unauthorized opening of the container or leaks from the container.

Figure 9:
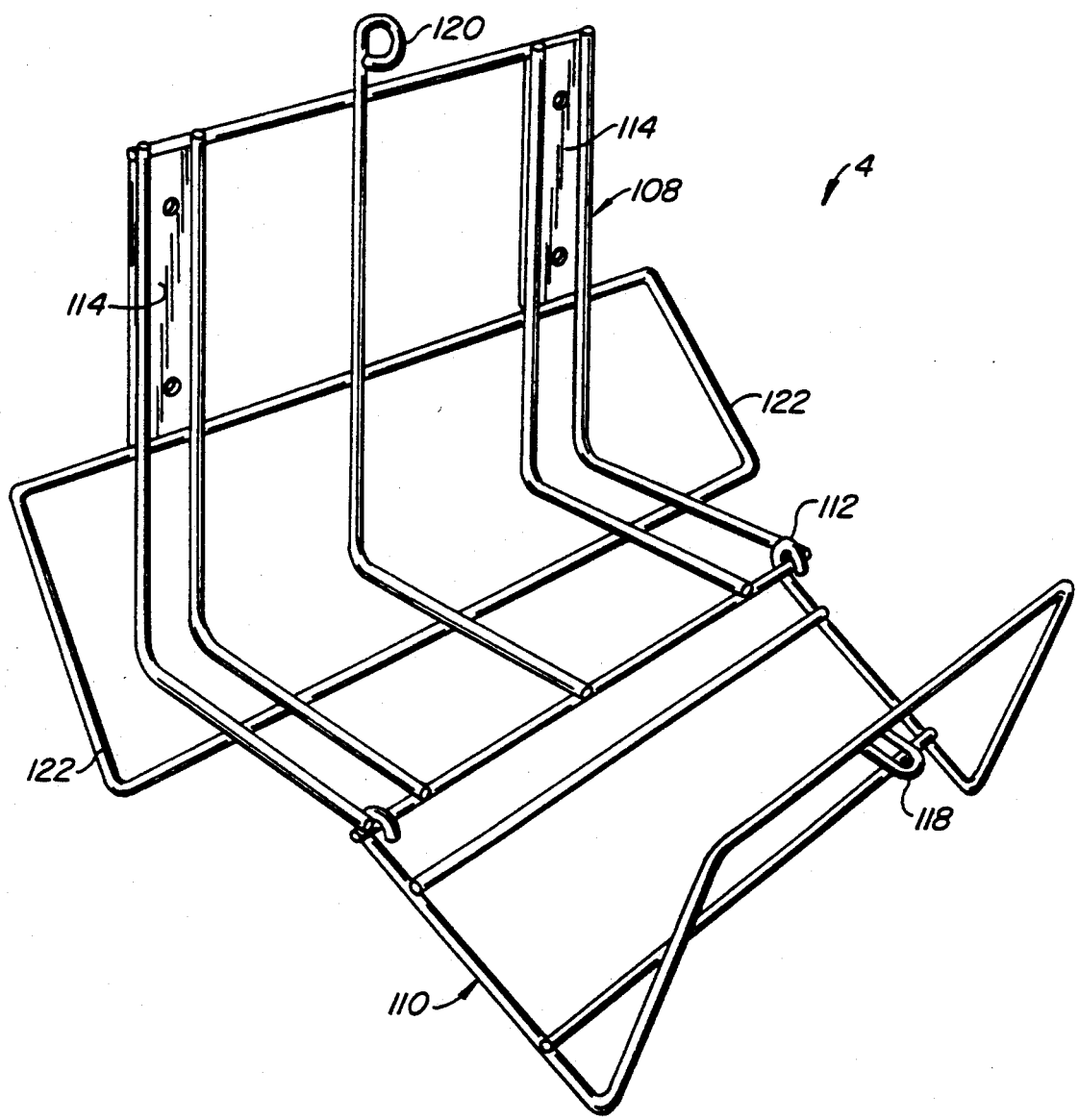
FIG. 9 is a perspective view of the cage of FIG. 1.

FIG. 9 shows cage 4 with container 6 removed therefrom. Cage 4 includes first and second L-shaped members 108, 110 hinged at 112 for movement between the opened, access position of FIG. 9 to the secured position of FIG. 1. Member 108 includes mounting bars 114 each having a pair of holes 116 formed therein for securing cage 4 to wall 8. Holes 116 are positioned so that when container 6 is mounted within cage 4, holes 116 are not accessible to deter unauthorized removal of the entire system 2. Cage 4 also includes end wire loops 118, 120 which serve as a hasp and staple to permit members 108, 110 to be locked together by a padlock 124. First member 108 also includes U-shaped extensions 122, which form the sides of cage 4, so that when cage 4 and container 6 are in the position of FIG. 1, container 6 is securely locked within the cage.

In use, cage 4 is mounted to wall 8, or other suitable support surface, using holes 116 and suitable fasteners. An empty container 6 is mounted within cage 4 and locked therein using padlock 124. Lid 84 is lifted away from top 22 to the position of FIG. 1 to expose entrance opening 70. Sharps, such as used syringes, vials, ampules and so forth, are disposed of within container 6 by dropping the sharps through entrance opening 70. When the medical debris within container 6 is to be disposed of, such as when the container is full as indicated by viewing the contents through view port 50 relative to fill line 54, protective liners 107 are removed from resilient sealing strips 104 and lid 84 is hinged downwardly against top 22 to secure the two together. After being so secured, padlock 124 is removed, second member 110 is pivoted away from first member 108 of cage 4 and container 6 is lifted safely from cage 4 using handles 126, which are integral extensions of top 22. Container 6 and the medical waste therein can then be disposed of, such as by incineration as a unit, without any additional handling of the medical waste or any plastic liner bags. This reduces the number of steps required in the disposal of sharps and reduces the possibility of inadvertent needle sticks during disposal as compared to other sharps disposal systems utilizing plastic liners.

Modifications and variations can be made to the disclosed embodiment without departing from the subject of the invention as defined in the following claims. For example, cage 4 could be made in a variety of shapes and configurations and, if desired, could be made of solid materials. Although container 6 is intended to be disposable, under appropriate circumstances it may be feasible to reuse the container.

What is claimed is:

1. A sharps disposal system comprising:
    a container including a circumference sidewall, a bottom and a top, the container defining an interior therein;
    the top including an entrance opening sized for deposit of sharps therethrough for containment within the interior of the container, said side wall having an inner surface extending downwardly from the top;
    the container including a baffle within the container and spaced below the entrance opening, said baffle having an inclined upper surface extending into the interior of the container and downwardly of the sidewall, the lower edge of the baffle being spaced inwardly of the inner surface of the sidewall to direct sharps dropped through the entrance opening into the interior;
    the container including a lid hinged to the top for movement between a stable open position, providing access to the entrance opening, and a stable closed position, covering the entrance opening to keep any sharps within the container, the lid having an inner peripheral surface adjacent the top when in the stable closed positions;
    the lid including a detented guide extending into the entrance opening throughout the movement of the lid between the stable open and closed positions, the detented guide having a detent region which engages the top in the stable open position;
    an adhesive seal for sealing the inner peripheral surface to the top so a substantially liquid-tight seal of the entrance opening can be created; and
    a container holder for securing the container to an object.

2. The system of claim 1 wherein the container is a rectangular box having a front side, a back side and lateral sides.

3. The system of claim 1 wherein the sidewall includes a view port to permit a user to visually inspect the contents of the container, at least the upper part of the view port being horizontally aligned with the baffel.

4. The system of claim 1 wherein the container is adapted to contain liquids which may leak from the sharps.

5. The system of claim 4 wherein the container includes an inside surface, the inside surface including a hydrophobic material.

6. The system of claim 1 wherein the container includes an absorbent material within the interior below the baffle to absorb liquids which may leak from the sharps.

7. The system of claim 1 wherein the container includes laterally extending handles for lifting the container.

8. The system of claim 7 wherein the handles are one-piece extensions of the top.

9. The system of clam 2 wherein the entrance opening includes a front edge, a rear edge and a guide flap extending from the front edge at an acute angle downwardly and rearwardly into the interior towards the bottom and the back side.

10. The system of claim 9 wherein the baffle includes a baffle surface extending from the back side below the guide flap, downwardly and forwardly towards the bottom and the front side.

11. The system of claim 2 wherein the baffle includes a baffle surface extending from the back side below the entrance opening, downwardly and forwardly towards the bottom and the front side.

12. The system of claim 1 wherein the adhesive seal includes a resilient seal.

13. The system of claim 1 wherein the container includes a tapered needle-separation slot formed therein.

14. The system of claim 1 wherein the needle-separation slot is formed in the top.

15. The system of claim 1 wherein the container is combustible.

16. The system of claim 15 wherein the container sidewall, top and bottom are made of fiberboard.

17. The system of claim 16 wherein the fiberboard is coated with a hydrophobic material facing the interior.

18. The system of claim 1 wherein the container holder comprises a wire cage configured to permit the lid to move between the open and closed positions so that the entrance opening can be sealed while the container is secured to the object by the container holder.

19. A sharps disposal system comprising:
    a combustible, rectangular, puncture-resistant fiberboard container including a circumference sidewall having a front side, a back side, lateral sides, a bottom and a top, the container defining an interior therein;
    the top including an entrance opening sized for deposit of sharps therethrough for containment within the interior of the container;
    the entrance opening including a front edge, a rear edge and a guide flap extending from the front edge at an acute angle downwardly and rearwardly into the interior towards the bottom and the back side;
    the container including a baffle within the interior positioned below the entrance opening to direct sharps dropped through the entrance opening into the interior, the baffle including an inclined upper surface extending from the back side below the guide flap, downwardly and forwardly towards the bottom and the front side;

the container including a lid hinged to the top for movement between a stable open position, providing access to the entrance opening, and a stable closed position, covering the entrance opening to keep any sharps within the container, the lid including an inner peripheral surface adjacent the top when in the stable closed position;

a resilient adhesive seal between the inner peripheral surface of the lid and the top so a substantially liquid-tight seal of the entrance opening can be created;

the lid including a detented guide extending into the entrance opening throughout the movement of the lid between the stable open and closed positions, the detented guide having detent regions which engage the top in the stable open and closed positions;

the container being adapted to contain liquids which may leak from the sharps;

the container including an absorbent material within the interior to absorb liquids which may leak from the sharps;

a view port formed in the front side to permit a user to visually inspect the contents of the container;

a lockable container holder for securing the container to an object;

the container including first and second laterally extending handles for lifting the container from the container holder, the handles being one-piece extensions of the top extending from opposite sides of the top.

20. A sharps disposal system comprising:

a container including a circumference sidewall, a bottom and a top, the container defining an interior therein;

the top including an entrance opening sized for deposit of sharps therethrough for containment within the interior of the container, said side wall having an inner surface extending downwardly from the top;

the container including a baffle within the container and spaced below the entrance opening, said baffle having an inclined upper surface extending into the interior of the container and downwardly of the sidewall, the lower edge of the baffle being spaced inwardly of the inner surface of the sidewall to direct sharps dropped through the entrance opening into the interior;

the container including a lid hinged to the top for movement between a stable open position, providing access to the entrance opening, and stable closed position, covering the entrance opening to keep any sharps within the container, the lid having an inner peripheral surface adjacent the top when in the stable closed position;

an adhesive seal for sealing the inner peripheral surface to the top so a substantially liquid-tight seal of the entrance opening can be created; and a container holder for securing the container to an object, the container holder comprising a wire cage, the wire cage including a first L-shaped part, configured to lie adjacent the back side and the bottom, a second L-shaped part hinged to the first part and configured to lie opposite the front side and the top and lockable to the first part, and side members, extending from at least one of the first and second parts, lying opposite the lateral sides.

21. The system of claim 20 wherein the first part includes mounting holes for securing the wire cage to a vertical surface.

* * * * *